US006682889B1

(12) United States Patent
Wang et al.

(10) Patent No.: US 6,682,889 B1
(45) Date of Patent: Jan. 27, 2004

(54) AMPLIFICATION AND DETECTION OF ORGANISMS OF THE CHLAMYDIACEAE FAMILY

(75) Inventors: Sha-Sha Wang, Cockysville, MD (US); David Wolfe, York, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/708,208

(22) Filed: Nov. 8, 2000

(51) Int. Cl.$^7$ ............................ C12Q 1/68; C12P 19/34; C07H 21/04

(52) U.S. Cl. ..................... 435/6; 435/91.2; 536/24.32; 536/24.33

(58) Field of Search ........................ 435/6, 91.2, 810; 536/24.32, 24.33

(56) References Cited

U.S. PATENT DOCUMENTS

| | | | |
|---|---|---|---|
| 5,232,829 A | 8/1993 | Longiaru et al. | 435/6 |
| 5,281,518 A | 1/1994 | Campbell et al. | 435/6 |
| 5,350,673 A | 9/1994 | Campbell et al. | 435/6 |
| 5,374,718 A | 12/1994 | Hammond et al. | 536/24.32 |
| 5,512,445 A | 4/1996 | Yang et al. | 435/6 |
| 5,514,551 A | 5/1996 | Yang et al. | 435/6 |
| 5,601,978 A | 2/1997 | Burczak et al. | 435/6 |
| 5,683,870 A | 11/1997 | Hammond et al. | 435/6 |
| 5,756,298 A | 5/1998 | Burczak et al. | 435/6 |
| 5,814,490 A | 9/1998 | Spears | 435/91.2 |
| 5,837,469 A | 11/1998 | Harris | 435/6 |
| 5,846,785 A | 12/1998 | Burczak et al. | 435/91.21 |
| 6,010,857 A | 1/2000 | Lee | 435/6 |
| 6,096,501 A | 8/2000 | Foxall et al. | 435/6 |
| 6,210,876 B1 | 4/2001 | Cerney | 435/6 |

FOREIGN PATENT DOCUMENTS

| | | |
|---|---|---|
| EP | 943691 A1 | 8/1999 |
| JP | 5317097 A | 12/1993 |
| JP | 8294400 A | 11/1996 |
| JP | 10262679 A | 10/1998 |
| RU | 2135516 C1 | 8/1999 |
| WO | 9810101 A1 | 3/1998 |
| WO | 9855646 A1 | 12/1998 |
| WO | 9927105 A2 | 6/1999 |
| WO | 9928475 A2 | 6/1999 |

OTHER PUBLICATIONS

Berger, M. et al. "Chlamydia pneumoniae DNA in Non–Coronary Atherosclerotic Plaques and Circulating Leukocytes" *J Lab Clin Med*. 2000. 136(3): 194–200.
Boman, J. et al. "Molecular Diagnosis of Chlamydia Pneumoniae Infection" *J Clin Microbiol*. 1999. 37(12): 3791–3799.
Brown, J. W. and Pace, N. R. "Ribonuclease P RNA and Protein Subunits From Bacteria" *Nucl. Acids Res*. 1992. 20(7): 1451–1456.
Campbell, L. A. et al. "Chlamydia pneumoniae and Cardiovascular Disease" *Emerg Infect Dis*. 1998. 4(4): 571–579.
Coombes, B. K. and Mahoney, J. B. "Nucleic Acid Sequence Based Amplification (NASBA) of Chlamydia pneumoniae Major Outer Membrane Protein (OMPA) MRNA With Bioluminescent Detection" *Comb Chem High Throughput Screen*. 2000. 3(4): 315–327.
Creelan, J. L., and McCullough, S. J. Evaluation of Strain–Specific Primer Sequences From an Abortifacient Strain of Ovine Chlamydophila abortus (Chalmydia psittaci) for the Detection of EAE by PCR. *FEMS Microbiol Lett*. 2000. 190(1): 103–108.
Dannatt, L. et al. "Investigation of a Possible Role for Chlamydia in a New Disease Syndrome in Dairy Cattle" *Veterin Rec*. 1998. 143 (25): 691–693.
Dille, B. J. et al. "Amplification of Chlamydia Trachomatis DNA by Ligase Chain Reaction" *J Clin Microbiol.*, 1993. 31(3): 729–731.
Everett, K. D. E. "Chlamydia and Chlamydiales: More Than Meets the Eye"0 *Veterin Microbiol*. 2000. 75(2): 109–126.
Everett, K. D. E. and Andersen, A. A. "Identification of Nine Species of the Chlamydiaceae Using PCR–RFLP" *Int J Syst Bacteriol*. 1999. 49: 803–813.
Everett, K. D. E. et al. "Emended Description of the Order Chlamydiales, Proposal of Parachlamydiaceae Fam. Nov. and Simkaniaceae Fam. Nov., Each Containing One Monotypic Genus, Revised Taxonomy of the Family Chlamydiaceae, Including a New Genus and Five New Species, and Standards for the Identification of Organisms" *Int J Syst Bacteriol*. 1999. 49: 415–440.
Everett, K. D. E. et al. "Rapid Detection of the Chlamydiaceae and Other Families in the Order Chlamydiales; Three PCR Tests" *J Clin Microbiol*. 1999. 37(3): 575–580.
Girjes, A. A. et al. "Single DNA Sequence Common to All Chlamydial Species Employed for PCR Detection of These Organisms" *Res Microbiol*. 1999. 150 (7): 483–489.
Haas, E. S. and Brown, J. W. "Evolutionary Variation in Bacterial RNASE P RNAS" *Nucl Acids Res*. 1998. 26(18): 4093–4099.
Herrmann, B. et al. "Characterization of the RNPB Gene and RNASE P RNA in the Order Chlamydiales" *Int J Syst Evol Microbiol*. 2000. 50: 149–158.
Herrmann, B. et al. "Differentiation of Chlamydia SPP. by Seqence Determination and Restriction Endonuclease Cleavage of RNASE P RNA Genes" *J Clin Microbiol*. 1996. 34(8): 1897–1902.
Hindiyeh, M. and Carroll, K. C. "Laboratory Diagnosis of Atypical Pneumonia" *Seminars Resp Infect*. 2000. 15(2): 101–113.

(List continued on next page.)

*Primary Examiner*—Kenneth R. Horlick
(74) *Attorney, Agent, or Firm*—Allan M. Kiang

(57) ABSTRACT

Amplification primers and methods for specific amplification and detection of a rnpB gene sequence are disclosed. The primer-target binding sequences are useful for amplification and detection of organisms of the Chlamydiaceae family in a variety of amplification and detection reactions.

31 Claims, 9 Drawing Sheets

OTHER PUBLICATIONS

Holland, S. M. et al. "Detection and Differentiation of *Chlamydia trachomatis, Chlamydia psittaci*, and *Chlamydia pneumoniae* by DNA Amplification" *J Infect Dis*. 1990. 162: 984–987.

Jantos, C. A. et al. "Rapid Detection of *Chlamydia pneumoniae* by PCR–Enzyme Immunoassay" *J Clin Microbiol*. 1998. 36(7): 1890–1894.

Jones, G. E. "Chlamydial Disease—More Than Just Abortion" *Veterin J*. 1997. 153(3): 249–251.

Kaltenböck, B. et al. "Evidence for Numerous *OMP1* Alleles of Porcine *Chlamydia trachomatis* and Novel Chlamydial Species Obtained by PCR" *J Clin Microbiol*. 1997. 35(7): 1835–1841.

Kuo, C. C. et al. "*Chlamydia pneumoniae* (TWAR)" *Clin Microbiol Rev*. 1995. 8(4): 451–461.

Madico, G. et al. "Touchdown Enzyme Time Release–PCR for Detection and Identification of *Chlamydia trachomatis, C. Pneumoniae*, and *C. Psittaci* Using the 16S and 16–23S Spacer RRNA Genes" *J Clin Microbiol*. 2000. 38(3): 1085–1093.

Mahony, J. B. et al. "Analytical Sensitivity, Reproducibility of Results, and Clinical Performance of Five PCR Assays for Detecting *Chlamydia pneumoniae* DNA in Peripheral Blood Mononuclear Cells" *J Clin Microbiol*. 2000. 38(7): 2622–7.

McDonald, M. et al. "A Comparison of DNA Amplification, Isolation and Seriology for the Detection of *Chlamydia psittaci* Infection in Cats" *Veterin Rec*. 1998. 143 (4): 97–101.

Messmer, T. O. et al. "Application of a Nested, Multiplex PCR to Psittacosis Outbreaks" *J Clin Microbiol*. 1997. 35(8): 2043–2046.

Odeh, M. and Oliven, A. "Chlamydial Infections of the Heart" *Eur J Clin Microbiol Infect Dis*. 1992. 11(10): 885–893.

Ramirez, J.A. et al. "Diagnosis of *Legionella pneumophila, Mycoplasma pneumoniae*, or *Chlamydia pneumoniae* Lower Respiratory Infection Using the Polymerase Chain Reaction on a Single Throat Swab Specimen" *Diagn Microbiol Infect Dis*. 1996. 24: 7–14.

Rasmussen, S. J. et al. "PCR Detection and Differentiation of *Chlamydia pneumoniae, C. psittaci*, and *C. trachomatis*" *Mol Cell Probes*. 1992. 6: 389–394.

Schachter, J. S. et al. "Ligase Chain Reaction to Detect *Chlamydia trachomatis* Infection of the Cervix" *J Clin Microbiol*. 1994. 32(10): 2540–2543.

Sheehy, N. et al. "Differentiation of *Chlamydia psittaci* and *C. pecorum* Strains by Species–Specific PCR" *J Clin Microbiol*. 1996. 34(12): 3175–3179.

Song, X. et al. "Quantitation of *Chlamydia trachomatis* 16S RRNA Using NASBA Amplification and a Bioluminescent Microtiter Plate Assay" *Comb Chem High Throughput Screen*. 2000. 3(4): 303–13.

Tong, C. Y. W. and Sillis, M. "Detection of *Chlamydia pneumoniae* and *C. psittaci* in Sputum Samples by PCR" *J Clin Pathol*. 1993. 46: 313–317.

FIG. 1  SDA schematic Diagram of detection of organisms of the Chlamydiaceae family with signal primer and reporter probe.
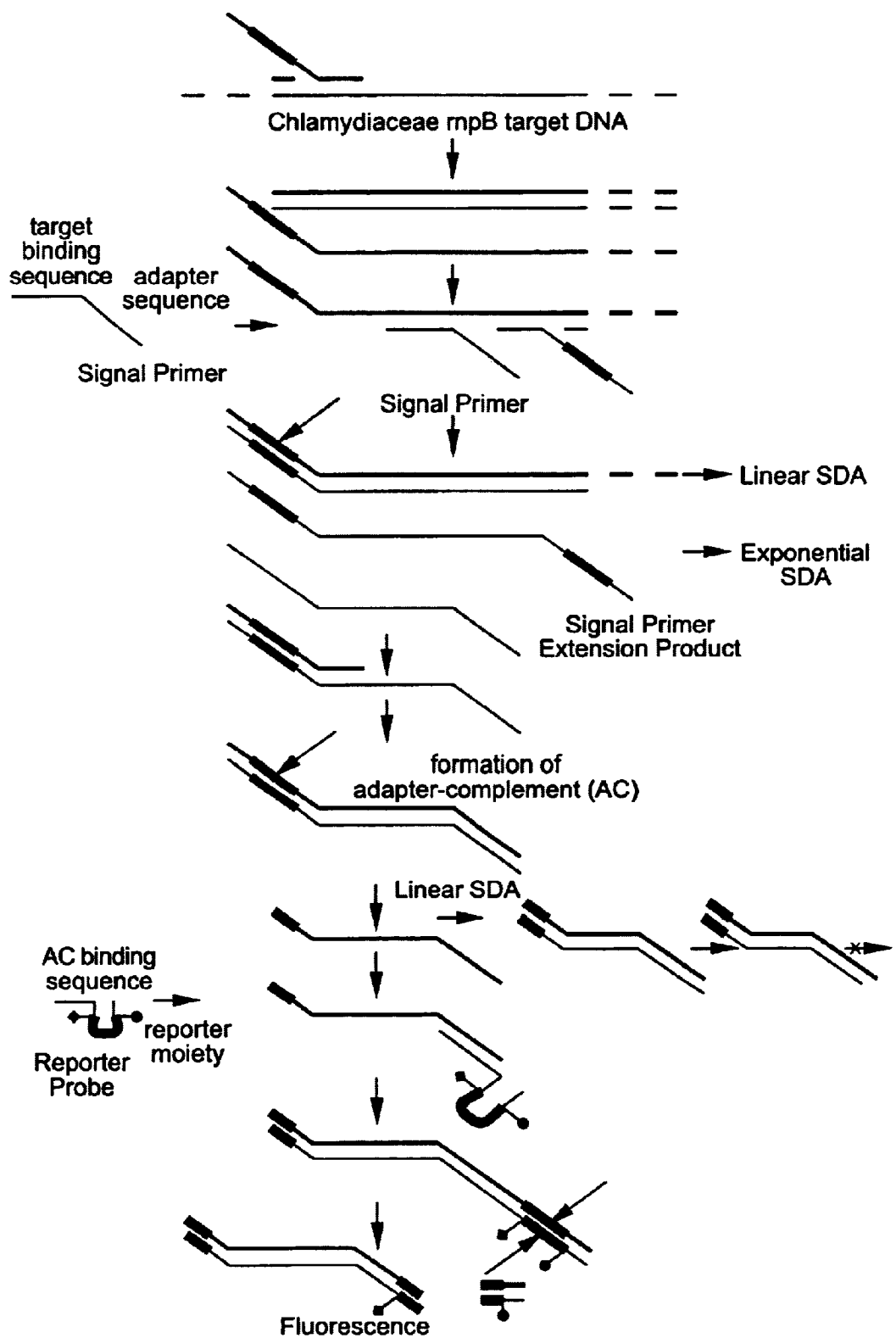

FIG. 2A Sequence alignment of SDA CG amplification oligonucleotides to Chlamydiaceae family *mpB* gene.

| | | | | | | | | | | | | |
|---|---|---|---|---|---|---|---|---|---|---|---|---|
| C C C T A T C T G A A G C A A G A G A A A A X X X X X X | | | | | | | | | | | | Majority |
| 160 170 180 | | | | | | | | | | | | |
| 151 . . . . . . . . . . . . . . . . . . . . . . . . . . . . . . | | | | | | | | | | | | U44033 C. pneumoniae.seq |
| 151 . . . . . . . . . . . . . . . . . . . . . . . . . . . A G | | | | | | | | | | | | AE001637 C. pneumoniae.seq |
| 151 . . . . . . . . . . . . . . . . . . . . . . . . . . . A G | | | | | | | | | | | | AE002183 C. pneumoniae.seq |
| 151 . . . . . C . . . . . . . . . . . . . . . . . . . A G C T T T T | | | | | | | | | | | | AP002547 C. pneumoniae.seq |
| 187 . . . . . C C . . . . . . . . . . . . . . . . . . . A G | | | | | | | | | | | | AJ012174 C. pneumoniae.seq |
| 153 . . . . . C C . . . . . . . . . . . . . . . . . . . A G | | | | | | | | | | | | U44031 C. trachomatis.seq |
| 153 . . . . . . . . . . . . . . . . . . . . . . . . . . . . . . | | | | | | | | | | | | AF056379 C. trachomatis.seq |
| 153 . . . . . . . . . . . . . . . . . . . . . . . . . . . . . . | | | | | | | | | | | | AJ131088 C. trachomatis.seq |
| 153 . . . . . . . . . . . . . . . . . . . . . . . . . . . . . . | | | | | | | | | | | | AJ012175 C. trachomatis.seq |
| 153 . . . . . . . . . . . . . . . . . . . . . . . . . . - G | | | | | | | | | | | | AJ012169 C. psittaci.seq |
| 154 . . . . . . . . . . . . . . . . . . . . . . . . . . - G | | | | | | | | | | | | AF056378 C. psittaci.seq |
| 153 . . . . . . . . . . . . . . . . . . . . . . . . . . - G | | | | | | | | | | | | AJ243523 C. psittaci.seq |
| 153 . . . . . C . . . . . . . . . . . . . . . . . . . . . . . | | | | | | | | | | | | U44032 C. psittaci.seq |
| 153 . . . . . . . . . . . . . . . . . . . . . . . . . . - G | | | | | | | | | | | | AJ012170 C. abortus.seq |
| 153 . . . . . . . . . . . . . . . . . . . . . . . . . . - G | | | | | | | | | | | | AJ012172 C. caviae.seq |
| 142 . . . . . . . . . . . . . . . . . . . . . . . . . . - G | | | | | | | | | | | | AJ012171 C. felis.seq |
| 153 . . . . . C . . . . . . . . . . . . . . . . . . . A G | | | | | | | | | | | | AJ012177 C. muridarum.seq |
| 153 . . . . . . . . . . . . . . . . . . . . . . . . . . A G | | | | | | | | | | | | AJ131089 C. pecorum.seq |
| 153 . . . . . . . . . . . . . . . . . . . . . . . . . . A G | | | | | | | | | | | | AJ131091 C. pecorum.seq |
| 153 . . . . . . . . . . . . . . . . . . . . . . . . . . . . . | | | | | | | | | | | | AJ012173 C. pecorum.seq |
| 153 . . . . . . . . . . . . . . . . . . . . . . . . . . . . . | | | | | | | | | | | | AJ012176 C. suis.seq |

Decoration 'Decoration #1': Hide (as '.') residues that match the Consensus exactly.

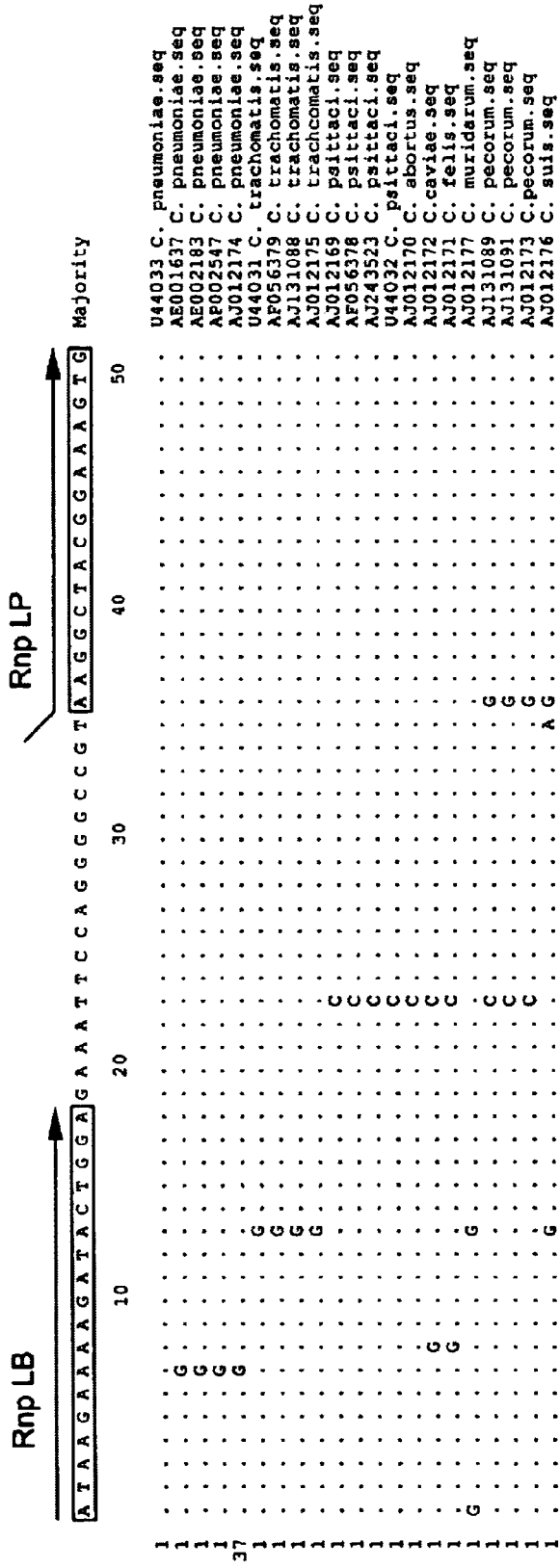
FIG. 3A Sequence alignment of SDA Rnp amplification oligonucleotides to Chlamydiaceae family *mpB* gene.

```
       C C C T A T C T G A A G C A A G A G A A A A A A X X X X X X X                Majority
                               160         170         180
                                                                          U44033   C. pneumoniae.seq
  151  . . . . . . . . . . . . . . . . . . . . . . . . . A G              AE001637 C. pneumoniae.seq
  151  . . . . . . . . . . . . . . . . . . . . . . . . . A .              AE002183 C. pneumoniae.seq
  151  . . . . . . . . . . . . . . . . . . . . . . . . . A G C T T T T    AP002547 C. pneumoniae.seq
  187  . . . . . . . . . . . . . . . . . . . . . . . . . A G              AJ012174 C. pneumoniae.seq
  153  . . . . C . . . . . . . . . . . . . . . . . . . .                  U44031   C. trachomatis.seq
  153  . . . . C . . . . . . . . . . . . . . . . . . . .                  AF056379 C. trachomatis.seq
  153  . . . . C . . . . . . . . . . . . . . . . . . . .                  AJ131088 C. trachomatis.seq
  153  . . . . . . . . . . . . . . . . . . . . . . . . . - G              AJ012175 C. trachomatis.seq
  153  . . . . . . . . . . . . . . . . . . . . . . . . . - G              AJ012169 C. psittaci.seq
  154  . . . . . . . . . . . . . . . . . . . . . . . . . - G              AF056378 C. psittaci.seq
  153  . . . . . . . . . . . . . . . . . . . . . . . . .                  AJ243523 C. psittaci.seq
  153  . . . . . . . . . . . . . . . . . . . . . . . . . - G              U44032   C. psittaci.seq
  153  . . . . . . . . . . . . . . . . . . . . . . . . . - G              AJ012170 C. abortus.seq
  142  . . . . C . . . . . . . . . . . . . . . . . . . .                  AJ012172 C.caviae.seq
  153  . . . . . . . . . . . . . . . . . . . . . . . . .                  AJ012171 C. felis.seq
  153  . . . . . . . . . . . . . . . . . . . . . . . . . A G              AJ012177 C. muridarum.seq
  153  . . . . . . . . . . . . . . . . . . . . . . . . . A G              AJ131089 C. pecorum.seq
  153  . . . . . . . . . . . . . . . . . . . . . . . . . A G              AJ131091 C. pecorum.seq
  153  . . . . C . . . . . . . . . . . . . . . . . . . .                  AJ012173 C.pecorum.seq
  153  . . . . . . . . . . . . . . . . . . . . . . . . .                  AJ012176 C. suis.seq
```

Rnp RB
Complimentary Seq.

Decoration 'Decoration #1': Hide (as '.') residues that match the Consensus exactly.

SEQUENCE LISTING

<160> NUMBER OF SEQ ID NOS: 11

<210> SEQ ID NO 1
<211> LENGTH: 38
<212> TYPE: DNA
<213> ORGANISM: Primer for SDA amplification of Chlamydiaceae

<400> SEQUENCE: 1
cgattccgct ccagacttct cgggtccagg ggccgtaa                              38

<210> SEQ ID NO 2
<211> LENGTH: 39
<212> TYPE: DNA
<213> ORGANISM: Primer for SDA amplification of Chlamydiaceae

<400> SEQUENCE: 2
accgcatcga atgactgtct cgggaaggct acggaaagt                             39

<210> SEQ ID NO 3
<211> LENGTH: 41
<212> TYPE: DNA
<213> ORGANISM: Primer for SDA amplification of Chlamydiaceae

<400> SEQUENCE: 3
accgcatcga atgactgtct cgggttcagc ctgtctataa a                          41

<210> SEQ ID NO 4
<211> LENGTH: 40
<212> TYPE: DNA
<213> ORGANISM: Primer for SDA amplification of Chlamydiaceae

<400> SEQUENCE: 4
cgattcagct gcagacgtct cgggttcagc ctgtctataa                            40

<210> SEQ ID NO 5

```
<211> LENGTH: 22
<212> TYPE: DNA
<213> ORGANISM: Bumper primer for SDA amplification of Chlamydiaceae

<400> SEQUENCE: 5
ataagaaaag atactgaaga aa                                            22

<210> SEQ ID NO 6
<211> LENGTH: 18
<212> TYPE: DNA
<213> ORGANISM: Bumper primer for SDA amplification of Chlamydiaceae

<400> SEQUENCE: 6
ataagaaaag atactgga                                                 18

<210> SEQ ID NO 7
<211> LENGTH: 15
<212> TYPE: DNA
<213> ORGANISM: Bumper primer for SDA amplification of Chlamydiaceae

<400> SEQUENCE: 7
gctcctactc ctaaa                                                    15

<210> SEQ ID NO 8
<211> LENGTH: 18
<212> TYPE: DNA
<213> ORGANISM: Bumper primer for SDA amplification of Chlamydiaceae

<400> SEQUENCE: 8
ttttctcttg cttcagat                                                 18

<210> SEQ ID NO 9
<211> LENGTH: 41
<212> TYPE: DNA
<213> ORGANISM: Signal primer for SDA amplification of Chlamydiaceae

<400> SEQUENCE: 9
acgttagcca ccatacggat ggctacggaa agtgcaacag a                       41

<210> SEQ ID NO 10
<211> LENGTH: 43
<212> TYPE: DNA
<213> ORGANISM: Signal primer for SDA amplification of Chlamydiaceae

<400> SEQUENCE: 10
acgttagcca ccatacggat acatagcgga gtgttttctg ttg                     43

<210> SEQ ID NO 11
<211> LENGTH: 35
<212> TYPE: DNA
<213> ORGANISM: Reproter probe for SDA amplification of Chlamydiaceae
<220> FEATURE:
<221> NAME/KEY: misc_feature
<222> LOCATION: (1)..(15)
<223> OTHER INFORMATION: T at position 1 is labeled with dabcyl;
      T at position 15 is labeled with rhodamin

<400> SEQUENCE: 11
tagtgcccga gcactacgtt agccaccata cggat                              35
```

US 6,682,889 B1

AMPLIFICATION AND DETECTION OF ORGANISMS OF THE CHLAMYDIACEAE FAMILY

FIELD OF THE INVENTION

The present invention relates to methods for determining the presence or absence of organisms of the Chlamydiaceae family in endocervical, throat and urethral swabs, urine, sputa, bronchoalveolar lavage fluids, eye secretions or other patient and animal specimens, cultures, food, and environmental samples. The method involves using nucleic acid primers to amplify specifically a target sequence within the ribonuclease P RNA gene (rnpB), preferably using one of the techniques of Strand Displacement Amplification (SDA), thermophilic Strand Displacement Amplification (tSDA) or fluorescent real time tSDA.

BACKGROUND OF THE INVENTION

Three species in the family Chlamydiaceae: *Chlamydophila pneumoniae* (formerly *Chlamydia pneumoniae*), *Chlamydia trachomatis* and *Chlamydophila psittaci* (formerly *Chlamydia psittaci*) (Everett, et al., 1999, *Int. J. Syst. Bacteriol.* 49:415–440), cause diseases in humans, which include trachoma; respiratory infection (pneumonia); and sexually transmitted infections of the reproductive organs, such as urethritis, cervicitis, pelvic inflammatory disease, and epididymitis. Pneumonia can be caused by *C. pneumoniae* and *C. psittaci* (psittacosis) in adults, and by *C. trachomatis* in newborn infants (Guo, et al., 1995, *Clin. Microbiol. Rev.* 8:451–461 and Madico, et al., 2000, *J. Clin. Microbiol.* 38(3):1085–1093). Some species of the Chlamydiaceae family may also be involved in infections of the heart (Odeh, et al., 1992, *Eur. J. Clin. Microbiol. Infect. Dis.* 11:885–893). The two genera in the family Chlamydiaceae, Chlamydia and Chlamydophila, include several species that can cause diseases in animals (Everett, et al., *Vet. Microbiol.* 75(2):109–126). Among these are, *C. psittaci* and *C. pecorum* which give rise to a wide variety of conditions in animals including abortion, pneumonia, enteritis, polyarthretis, encephalomyelitis, and conjunctivitis (Sheehy, et al., 1996, *J. Clin. Microbiol.* 34(2):3175–3179). There is therefore a clinical need for the detection of all pathogens or potential pathogens within the Chlamydiaceae in a variety of clinical samples.

Endoribonuclease P (RNase P) is a ribonucleoprotein complex that removes 5' leader sequences from tRNA precursors during tRNA biosynthesis. RNase P is an essential riboenzyme found in all living cells and subcellular compartments that synthesize tRNA, although catalytic proficiency of the RNA alone has been demonstrated only for the bacterial RNase P (Brown, et al., 1992, *Nucl. Acids Res.* 20:1451–1456 and Haas, et al., 1998, *Nucl. Acids Res.* 26:4093–4099). Sequencing of the RNase P RNA genes provides a potential tool for the identification of bacteria and eukaryotic organisms in clinical diagnostics. The RNase P RNA gene (rnpB) has recently been used as a marker to differentiate chlamydial strains and species (Herrmann, et al., 1996, *J. Clin. Microbiol.* 34(8):1897–1902). Characterization of the rnpB gene in the order Chlamydiales (Herrmann, et al., 2000, *Int. J. Syst. Evol. Microbiol.* 50:149–158) revealed similarities of 76.6% between *C. trachomatis* and *C. pneumoniae*, 79.5% between *C. trachomatis* and *C. psittaci*, and 84.7% between *C. pneumoniae* and *C. psittaci*. It is therefore possible to use the rnpB gene as a genus or familial marker to identify organisms within the Chlamydiaceae.

Nucleic acid amplification is a powerful technology, which allows rapid detection of specific target sequences and it is therefore a promising technology for the rapid detection and identification of species in the Chlamydiaceae family. Various nucleic acid amplification methods have been described previously for the detection of some or all of the species within this group of organisms. Touchdown enzyme time release-PCR has been used to amplify specific DNA sequences in the variable regions of the 16S and 16–23S spacer rRNA genes of *C. trachomatis*, *C. pneumoniae*, and *C. psittaci* (Madico, et al., 2000, *J. Clin. Microbiol.* 38:1085–1093). Rapid detection of the Chlamydiaceae and other families in the order Chlamydiales has also been reported using three different PCR assays targeting the ompA gene and the rRNA intergenic spacer region (Everett, et al., 1999, *J. Clin. Microbiol.* 37:575–580). Identification of nine species of the Chlamydiaceae using PCR-Restriction Fragment Length Polymorphism analysis was also reported by Everett, et al. (1999, *Int. J. Syst. Bacteriol.* 49:803–813), and Jantos, et al. described detection of *C. pneumoniae* using a PCR-enzyme immunoassay based on the 16S rRNA gene (1998, *J. Clin. Microbiol.* 36:1890–1894). Kaltenböck, et al. established a nested PCR for genus-specific amplification of the Chlamydia omp1 locus (1997, *J. Clin. Microbiol.* 35:1835–1841) and the application of a nested, multiplex PCR based on the 16S rRNA gene, in the investigation of psittacosis outbreaks was reported by Messmer, et al. (1997, *J. Clin. Microbiol.* 35:2043–2046). Differentiation of *C. psittaci* and *C. pecorum* by species-specific PCR targeting the outer membrane protein genes has been reported by Sheehy, et al. (1996, *J. Clin. Microbiol.* 34:3175–3179). Use of the ligase chain reaction (LCR) has also been described for the amplification and detection of *C. trachomatis* (Dille, et al., 1993, *J. Clin. Microbiol.* 31:729–731 and Schachter, et al., 1994, *J. Clin. Microbiol.* 32:2540–2543). The oligonucleotide primers of the present invention are applicable to nucleic acid amplification and detection of organisms belonging to the Chlamydiaceae family.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease, which will nick one strand of a DNA duplex, when the recognition site is hemimodified, as described by G. Walker, et al. (1992. *Proc. Natl. Acad. Sci. USA* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified. As the target binding sequence is the portion of a primer which determines its target-specificity, for amplification methods which do not require specialized sequences at the ends of the target the amplification primer generally consists essentially of only the target binding sequence. For example, amplification of a target sequence according to the invention using the Polymerase Chain Reaction (PCR) will employ amplification primers consisting of the target binding sequences of the amplification primers described herein. For amplification methods that require specialized sequences appended to the target other than the nickable restriction endonuclease recognition site and the tail of SDA (e.g., an RNA polymerase promoter for Self-Sustained Sequence Replication (3SR), Nucleic Acid Sequence-Based Amplification (NASBA) or the Transcription-Based Amplification System (TAS)), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence that are generated during the amplification reaction are referred to as amplification products, amplimers or amplicons.

The term extension product refers to the copy of a target sequence produced by hybridization of a primer and extension of the primer by polymerase using the target sequence as a template.

The term family-specific refers to detection, amplification or oligonucleotide hybridization to organisms of species belonging to a family without substantial detection, amplification or oligonucleotide hybridization to other organisms of species belonging to a different family.

The term assay probe refers to any oligonucleotide used to facilitate detection or identification of a nucleic acid. Detector probes, detector primers, capture probes, signal primers and reporter probes as described below are examples of assay probes.

A signal primer comprises a 3' target binding sequence that hybridizes to a complementary sequence in the target and further comprises a 5' tail sequence that is not complementary to the target (the adapter sequence). The adapter sequence is an indirectly detectable marker selected such that its complementary sequence will hybridize to the 3' end of the reporter probe described below. The signal primer hybridizes to the target sequence at least partially downstream of the hybridization site of an amplification primer. The signal primer is extended by the polymerase in a manner similar to extension of the amplification primers. Extension of the amplification primer displaces the extension product of the signal primer in a target amplification-dependent manner, producing a single-stranded product comprising a 5' adapter sequence, a downstream target binding sequence and a 3' binding sequence specific for hybridization to a flanking SDA amplification primer. Hybridization and extension of this flanking amplification primer and its subsequent nicking and extension creates amplification products containing the complement of the adapter sequence which may be detected as an indication of target amplification.

A reporter probe according to the present invention functions as a detector oligonucleotide and comprises a label which is preferably at least one donor/quencher dye pair, i.e., a fluorescent donor dye and a quencher for the donor fluorophore. The label is linked to a sequence or structure in the reporter probe (the reporter moiety) which does not hybridize directly to the target sequence. The sequence of the reporter probe 3' to the reporter moiety is selected to hybridize to the complement of the signal primer adapter sequence. In general, the 3' end of the reporter probe does not contain sequences with any significant complementarity to the target sequence. If the amplification products containing the complement of the adapter sequence described above are present, they can then hybridize to the 3' end of the reporter probe. Priming and extension from the 3' end of the adapter complement sequence allows the formation of the reporter moiety complement. This formation renders the reporter moiety double-stranded, thereby allowing the label of the reporter probe to be detected and indicating the presence of or the amplification of the target.

The term amplicon refers to the product of the amplification reaction generated through the extension of either or both of a pair of amplification primers. An amplicon may contain exponentially amplified nucleic acids if both primers utilized hybridize to a target sequence. Alternatively, amplicons may be generated by linear amplification if one of the primers utilized does not hybridize to the target sequence. Thus, this term is used generically herein and does not imply the presence of exponentially amplified nucleic acids.

SUMMARY OF THE INVENTION

The present invention provides oligonucleotide primers that can be used for amplification of a target sequence found in the species of the family Chlamydiaceae. More specifically, the target sequence comprises segments of the rnpB gene. The amplification primers have been designed for high-efficiency, high-specificity amplification at elevated temperatures, such as in tSDA and the PCR, however, they are also useful in lower-temperature amplification reactions such as conventional SDA, 3SR, TAS or NASBA. An oligonucleotide reporter probe that hybridizes to the complement of target specific signal primers is used to indirectly detect the amplification products.

The oligonucleotides of the invention may be used with clinical samples from humans, such as endocervical, throat and urethral swabs, urine, sputa, bronchoalveolar lavage fluids, eye secretions or with other patient and animal specimens, cultures, food, and environmental samples, for detection and identification of nucleic acid from organisms belonging to the Chlamydiaceae family using known amplification methods. The inventive oligonucleotides and assay methods provide a means for rapidly discriminating between the species of the family Chlamydiaceae and other microorganisms, allowing the practitioner to identify these microorganisms rapidly without resorting to the more traditional procedures customarily relied upon. Since human respiratory infections caused by *C. pneumoniae*, neonatal pneumonia caused by *C. trachomatis* and psittacosis caused by *C. psittaci* organisms can all be treated with the same antibiotic therapy, a Chlamydiaceae family-specific assay has significant clinical value. Rapid identification of an etiological agent belonging to the Chlamydiaceae family provides information within a short period of time that can be used to determine appropriate therapeutic action.

SUMMARY OF THE SEQUENCES

SEQ ID NOs: 1–2 are the sequences of oligonucleotides used as upstream primers for amplification of the rnpB gene. SEQ ID NOs: 3–4 are the sequences of oligonucleotides used as downstream primers for amplification of the rnpB gene. SEQ ID NOs: 5–6 are the sequences of oligonucleotides used as upstream bumpers for SDA amplification. SEQ ID NOs: 7–8 are the sequences of oligonucleotides used as downstream bumpers for SDA amplification. SEQ ID NOs: 9–10 are the sequences of signal primers for amplification and detection of sequences within the rnpB gene. SEQ ID NO: 11 is a sequence for a reporter probe designed for detection of a sequence within the rnpB gene when used in conjunction with any of the aforementioned signal primers.

BRIEF DESCRIPTION OF THE DRAWING

The various objects, advantages and novel features of the present invention will be readily understood from the following detailed description when read in conjunction with the appended drawing in which:

FIG. 1 illustrates detection of a family Chlamydiaceae nucleic acid rnpB target sequence in a Strand Displacement Amplification (SDA) reaction according to the method of the invention.

are known to those skilled in the art from references such as U.S. Pat. No. 5,547,861, U.S. Pat. No. 5,648,211, U.S. Pat. No. 5,846,726, U.S. Pat. No. 5,919,630, U.S. Pat. No. 5,928,869, U.S. Pat. No. 5,958,700, U.S. Pat. No. 5,935,791, U.S. Pat. No. 6,054,279, U.S. Pat. No. 6,130,047, U.S. patent application Ser. No. 09/590,061, filed Jun. 8, 2000, U.S. Pat. No. 6,316,200, and U.S. patent application Ser. No. 09/602,996, filed Jun. 23, 2000, U.S. Pat. No. 6,258,546, the disclosures of which are hereby specifically incorporated herein by reference.

Figure 2B:
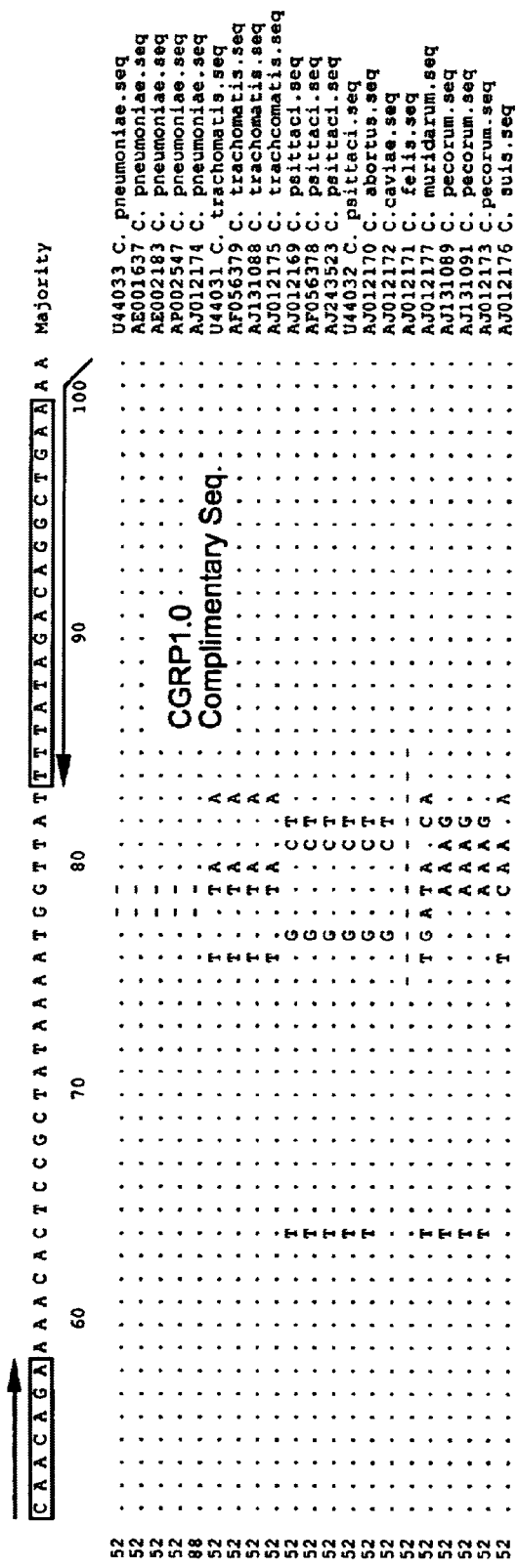
FIG. 2 illustrates the alignment of the target binding sequences of SEQ ID NOs: 1, 3, 5, 7 and 9 in SDA amplification of the rnpB gene from several Chlamydiaceae family species and strains.
Figure 2C:
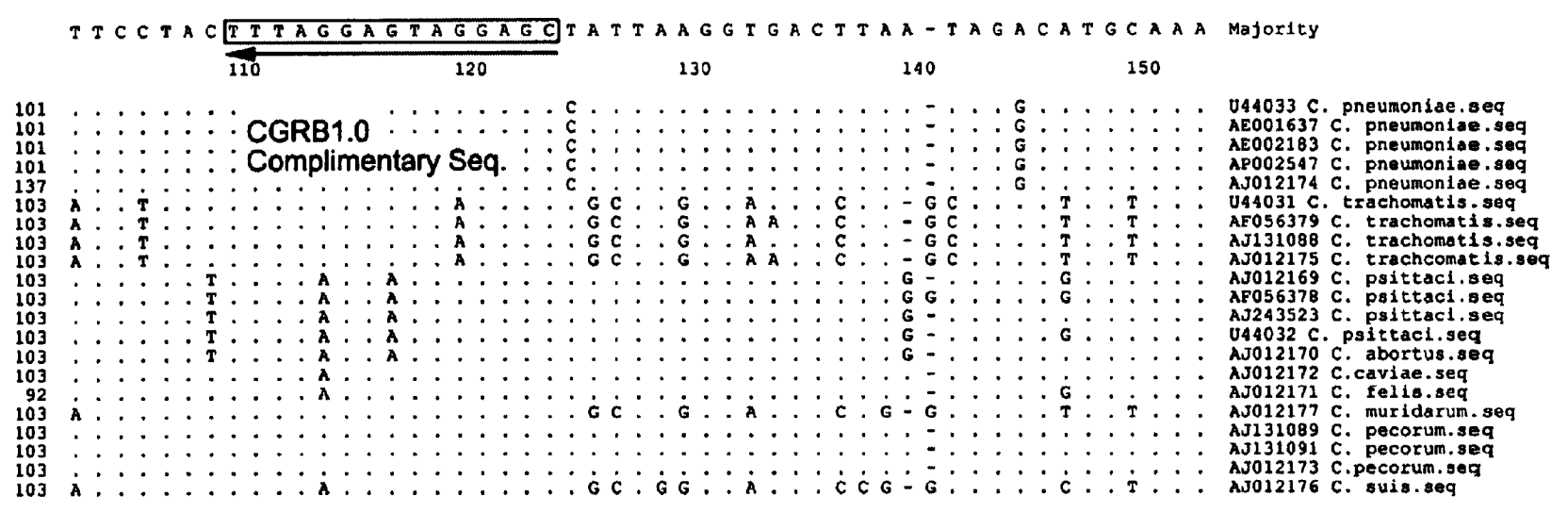
Figure 3B:
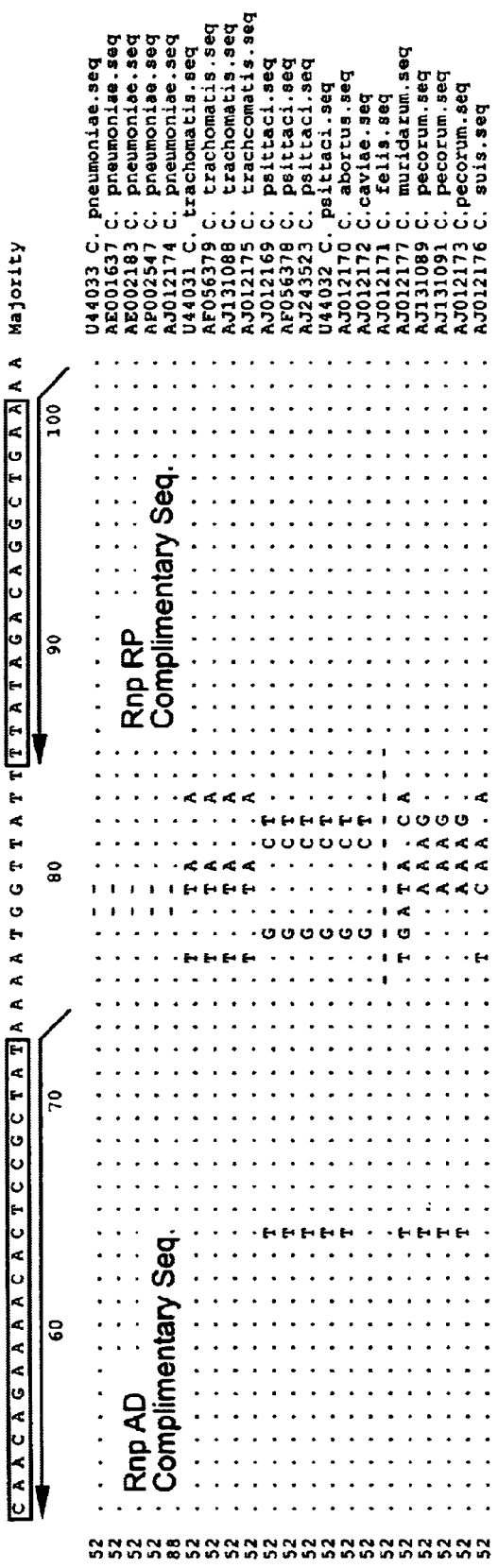
FIG. 3 illustrates the alignment of the target binding sequences of SEQ ID NOs: 2, 4, 6, 8 and 10 in SDA amplification of the rnpB gene from several Chlamydiaceae family species and strains.
Figure 3C:
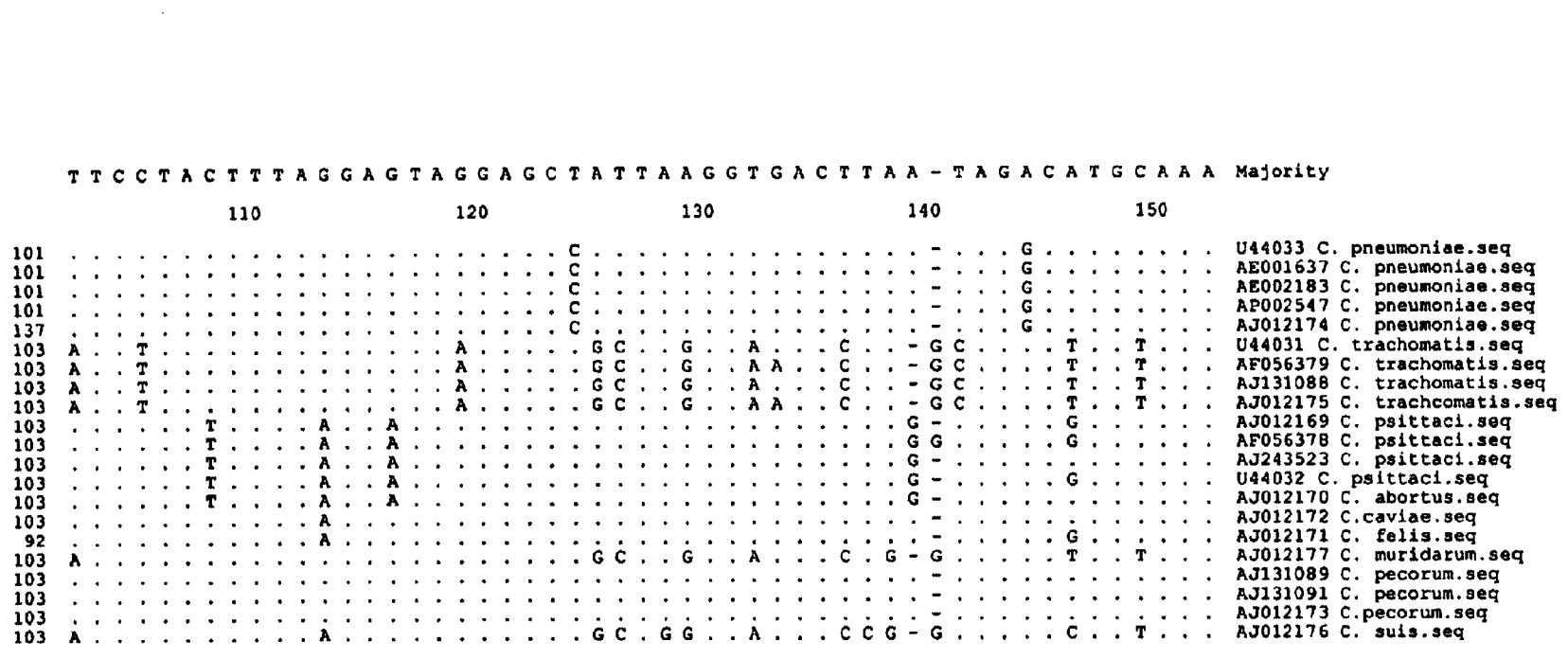

The primers of the present invention were designed based on an analysis of rnpB gene sequence data from multiple sources that were aligned to identify Chlamydiaceae-specific regions, as illustrated in FIGS. 2 and 3. The primers developed for use in tSDA are shown in Table 1. The exemplary restriction endonuclease recognition sites (BsoBI) in the amplification primers are shown in boldface type and the target binding sequences are italicized. Also shown are signal primers and a reporter probe for the amplification and detection of the resultant amplicons. The target binding sequence of an amplification primer determines its target specificity. As illustrated in FIGS. 2 and 3, the target binding sequences of the designed upstream primers, bumpers and signal primer CGA 1.0 (SEQ ID NO: 9) share the same nucleotide sequence with rnpB gene nucleotides that are boxed. The complements of the target binding sequences of the designed downstream primers, bumpers and signal primer Rnp AD (SEQ ID NO: 10) share the same nucleotide sequence with rnpB gene nucleotides that are boxed. The designed primers will amplify a target sequence that is present in all species of the Chlamydiaceae Family except for the species *C. felis* which has been associated with rare zoonotic infection in humans.

TABLE 1

| Amplification Oligonucleotides |
| --- |
| Upstream Primers |
| CGLP1.0:5'-CGATTCCGCTCCAGACTTCTCGGG*TCCAGGGGCCGTAA*(SEQ ID NO: 1) |
| Rnp LP:5'-ACCGCATCGAATGACTGTCTCGGG*AAGGCTACGGAAAGT*(SEQ ID NO: 2) |
| Downstream Primers |
| CGRP1.0:5'-ACCGCATCGAATGACTGTCTCGGG*TTCAGCCTGTCTATAAA*(SEQ ID NO: 3) |
| Rnp RP:5'-CGATTCAGCTGCAGACGTCTCGGG*TTCAGCCTGTCTATAA*(SEQ ID NO: 4) |
| Upstream Bumpers |
| CGLB1.0: 5'-ATAAGAAAAGATACTGAAGAAA (SEQ ID NO: 5) |
| Rnp LB: 5'-ATAAGAAAAGATACTGGA (SEQ ID NO: 6) |
| Downstream Bumpers |
| CGRB1.0: 5'-GCTCCTACTCCTAAA (SEQ ID NO: 7) |
| Rnp RB: 5'-TTTTCTCTTGCTTCAGAT (SEQ ID NO: 8) |
| Signal Primers |
| CGA1.0: 5'-ACGTTAGCCACCATACGGATGGC*TACGGAAAGTGCAACAGA*(SEQ ID NO: 9) |
| Rnp AD: 5'-ACGTTAGCCACCATACGGATACA*TAGCGGAGTGTTTTCTGTTG*(SEQ ID NO: 10) |
| Reporter Probe |
| TBD10: 5'-(dabcyl)TAGTGCCCGAGCACT(rhodamine)ACGTTAGCCACCATACGGAT (SEQ ID N0: 11) |

DETAILED DESCRIPTION OF THE INVENTION

The present invention relates to oligonucleotides, amplification primers and signal primers that exhibit specificity for organisms of the Chlamydiaceae family in nucleic acid amplification reactions. Also provided are methods for detecting and identifying nucleic acids from organisms of the Chlamydiaceae family using the oligonucleotides of the invention. The preferred methods are to use SDA, tSDA or homogeneous real time fluorescent tSDA. These methods As nucleic acids do not require complete complementarity in order to hybridize, it is to be understood that the probe and primer sequences herein disclosed may be modified to some extent without loss of utility as rnpB specific probes and primers. As is known in the art, hybridization of complementary and partially complementary nucleic acid sequences may be obtained by adjustment of the hybridization conditions to increase or decrease stringency (i.e., adjustment of hybridization pH, temperature or salt content of the buffer). Such minor modifications of the disclosed sequences and any necessary adjustments of hybridization conditions to maintain specificity for the organisms of the Chlamydiaceae family require only routine experimentation and are within the ordinary skill in the art.

The amplification products generated using the primers disclosed herein may be detected by a characteristic size, for example, on polyacrylamide or agarose gels stained with ethidium bromide. Alternatively, amplified target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al. (1992, *Nucl. Acids Res.* 20:1691–1696) (a detector primer) or by hybridization, extension and conversion to double stranded form as described in EP 0 678 582 (a signal primer).

A preferred embodiment for the detection of amplified target is illustrated schematically in FIG. 1. In this embodiment, the 5' tail sequence of the signal primer is comprised of a sequence that does not hybridize to the target (the adapter sequence). The adapter sequence is an indirectly detectable marker that may be selected such that it is the same in a variety of signal primers that have different 3' target binding sequences (i.e., a "universal" 5' tail sequence). Oligonucleotides having SEQ ID NOs: 9 and 10 are particularly useful as signal primers, in conjunction with the amplification primers of the invention, for detection of organisms of the Chlamydiaceae family. Preferably, an assay probe is a single reporter probe sequence that hybridizes to the adapter sequence complement of the signal primers of the invention. An oligonucleotide having SEQ ID NO: 11 is particularly useful as a reporter probe when used in conjunction with the signal primers of the invention for detection of organisms of the Chlamydiaceae family. Alternatively, an assay probe can be selected to hybridize to a sequence in the target that is between the amplification primers. In a further embodiment, an amplification primer or the target binding sequence thereof may be used as the assay probe.

The detectable label of the assay probe is a moiety that can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label that requires additional reagents to render it detectable. Indirectly detectable labels include, for example, chemiluminescent agents, enzymes that produce visible reaction products and ligands (e.g., haptens, antibodies or antigens) which may be detected by binding to labeled specific binding partners (e.g., antibodies or antigens/haptens). Ligands are also useful for immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In yet another alternative for detection of amplification products, the signal primer may contain sequences that do not hybridize to the target sequence, i.e., the adapter sequence. In this embodiment, as illustrated in FIG. 1, a reporter probe with associated label can hybridize to the complement of the adapter sequence. In both embodiments of the signal primer, secondary amplification products are generated during SDA in a target amplification-dependent manner and may be detected as an indication of target amplification.

For commercial convenience, amplification primers for specific detection and identification of nucleic acids may be packaged in the form of a kit. Typically, such a kit contains at least one pair of amplification primers. Reagents for performing a nucleic acid amplification reaction may also be included with the target-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

For the present invention, such a kit may be configured in order to provide the necessary components for a respiratory panel of organisms. Such a respiratory panel may include *Bordetella pertussis, Legionella pneumophila, Mycoplasma pneumoniae* and family Chlamydiaceae organisms in addition to other microorganisms capable of causing respiratory infection. Thus, such a respiratory panel kit would include the primers for amplification of a nucleic acid sequence specific for each of the organisms of the respiratory panel. Useful primers, bumpers, signal primers and reporter probes for amplifying and detecting *B. pertussis, L. pneumophila* and *M. pneumoniae* are described in U.S. patent application Ser. No. 09/626,855, filed on Jul. 27, 2000, U.S. Pat. No. 6,261,785, U.S. patent application Ser. No. 09/626,354, filed on Jul. 27, 2000 U.S. Pat. No. 6,251,609, and U.S. patent application Ser. No. 09/626,355, filed on Jul. 27, 2000, U.S. Pat. No. 6,277,582, respectively the disclosures of which are specifically incorporated herein by reference. When used, such a respiratory panel kit may permit separate amplification reactions for each organism or one or more multiplex amplification reactions to provide results indicating the presence or absence of each of the organisms of the panel.

The target binding sequences of the amplification primers confer species hybridization specificity on the oligonucleotides and therefore provide species specificity to the amplification reaction. Thus, the target binding sequences of the amplification primers of the invention are also useful in other nucleic acid amplification protocols such as PCR, conventional SDA (a reaction scheme which is essentially the same as that of tSDA but conducted at lower temperatures using mesophilic enzymes), 3SR, NASBA and TAS. Specifically, any amplification protocol which utilizes cyclic, specific hybridization of primers to the target sequence, extension of the primers using the target sequence as a template and separation or displacement of the extension products from the target sequence may employ the target binding sequences of the invention. For amplification methods that do not require specialized, non-target binding sequences (e.g., PCR), the amplification primers may consist essentially of the target binding sequences of the amplification primers listed in Table 1.

Other sequences, as required for performance of a selected amplification reaction, may optionally be added to the target binding sequences disclosed herein without altering the species specificity of the oligonucleotide. By way of example, the specific amplification primers may contain a recognition site for the restriction endonuclease BsoBI that is nicked during the SDA reaction. It will be apparent to one skilled in the art that other nickable restriction endonuclease recognition sites may be substituted for the BsoBI recognition site including, but not limited to, those recognition sites disclosed in EP 0 684 315. Preferably, the recognition site is for a thermophilic restriction endonuclease so that the amplification reaction may be performed under the conditions of tSDA. Similarly, the tail sequence of the amplification primer (5' to the restriction endonuclease recognition site) is generally not critical, although the restriction site used for SDA and sequences which will hybridize either to their own target binding sequence or to the other primers should be avoided. Some amplification primers for SDA therefore consist of 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. As described in U.S. patent application Ser. No. 09/573,242, filed May 18, 2000, some amplification primers for SDA can consist of target specific sequences both 5' and 3' of the restriction enzyme recognition site. An increase in the efficiency of target specific hybridization may be attained with this design. For other amplification reactions (e.g., 3SR, NASBA and TAS), the amplification primers may consist of the target binding sequence and additional sequences required for the selected amplification reaction (e.g., sequences required for SDA as described above or a promoter recognized by RNA polymerase for 3SR). Adaptation of the target binding sequences of the invention to amplification methods other than SDA employs routine methods for preparation of amplification primers, such as chemical synthesis, and the well known structural requirements for the primers of the selected amplification reaction. The target binding sequences of the invention may therefore be readily adapted to provide specific amplification and detection of organisms of the Chlamydiaceae family in a variety of amplification reactions using only routine methods for production, screening and optimization.

In SDA mediated detection of organisms of the Chlamydiaceae family, the bumper primers are not essential for family specificity, as they function to displace the downstream, family-specific amplification primers. It is required only that the bumper primers hybridize to the target upstream from the amplification primers so that when they are extended they will displace the amplification primer and its extension product. The particular sequence of the bumper primer is therefore generally not critical, and may be derived from any upstream target sequences which are sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence.

Amplification reactions employing the primers of the invention may incorporate thymine as taught by Walker, et al. (1992, *Nucl. Acids Res.* 20:1691–1696), or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (UGI) prior to performing the subsequent amplification to prevent excision of dU in newly-formed amplification products.

SDA is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate α-thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others that display the required nicking activity are suitable for use in conventional SDA. However, they are relatively thermolabile and lose activity above about 40° C.

Targets for amplification by SDA may be prepared by fragmenting larger nucleic acids by restriction with an endonuclease that does not cut the target sequence.

However, it is generally preferred that target nucleic acids having selected restriction endonuclease recognition/cleavage sites for nicking in the SDA reaction be generated as described by Walker, et al. (1992, *Nucl. Acids Res.* 20:1691–1696) and in U.S. Pat. No. 5,270,184 (specifically incorporated herein by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next iteration of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA iteration and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with UGI prior to amplification of the target. Alternatively, UDG may be heat-inactivated. In tSDA, the higher temperature of the reaction itself ($\geq 50°$ C.) can be used concurrently to inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence that can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity of the restriction enzyme is also of great importance, as it is nicking which perpetuates the reaction and allows subsequent rounds of target amplification to initiate.

tSDA is performed essentially as the conventional SDA described by Walker, et al. (1992, *Proc. Natl. Acad. Sci. USA* 89:392–396 and 1992, *Nucl. Acids Res.* 20:1691–1696), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in tSDA are BsrI, BstNI, BsmAI, BslI and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable by a restriction endonuclease. Cleavage by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

A detector oligonucleotide for homogeneous real time fluorescent tSDA may be an oligonucleotide which comprises both a single-stranded 5' or 3' section which hybridizes to the target sequence (the target binding sequence), as well as an intramolecularly base-paired secondary structure adjacent to the target binding sequence. In a preferred embodiment, as illustrated in FIG. 1, the detector oligonucleotide is a reporter probe that comprises a single-stranded 5' or 3' section that does not hybridize to the target sequence. Rather, the single-stranded 5' or 3' section hybridizes to the complement of the signal primer adapter sequence (the adapter-complement binding sequence). A further characteristic of the reporter probe is that this hybridizing section is adjacent to an intramolecularly base-paired secondary structure. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching.

The detector oligonucleotides of the invention for homogeneous real time fluorescent tSDA comprise a sequence that forms an intramolecularly base-paired secondary structure under the selected reaction conditions for primer extension or hybridization. In one embodiment, the secondary structure may be positioned adjacent to the target binding sequence of the detector oligonucleotide so that at least a portion of the target binding sequence forms a single-stranded 3' or 5' tail. In a preferred embodiment, as illustrated in FIG. 1, the secondary structure is positioned adjacent to the adapter-complement binding sequence of the reporter probe detector oligonucleotide so that at least a portion of the adapter-complement binding sequence forms a single-stranded 3' or 5' tail. As used herein, the term "adjacent to the target binding sequence" or "adjacent to the adapter-complement binding sequence" means that all or part of the target/adapter-complement binding sequence is left single-stranded in a 5' or 3' tail which is available for hybridization to the target/adapter-complement. That is, the secondary structure does not comprise the entire target/adapter-complement binding sequence. A portion of the target/adapter-complement binding sequence may be involved in the intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target/adapter-complement binding sequence of the detector oligonucleotide is present as a single-stranded 3' tail, the target/adapter-complement binding sequence may also extend through all or part of the first arm of the stem and, optionally, through all or part of the loop. However, the target/adapter-complement binding sequence preferably does not extend into the second arm of the sequence involved in stem intramolecular base-pairing. That is, it is desirable to avoid having both sequences involved in intramolecular base-pairing in a secondary structure capable of hybridizing to the target/adapter-complement. Mismatches in the intramolecularly base-paired portion of the detector oligonucleotide secondary structure may reduce the magnitude of the change in fluorescence in the presence of target but are acceptable if assay sensitivity is not a concern. Mismatches in the target/adapter-complement binding sequence of the single-stranded tail are also acceptable but may similarly reduce assay sensitivity and/or specificity. However, it is a feature of the present invention that perfect base-pairing in both the secondary structure and the target/adapter-complement binding sequence do not compromise the reaction. Perfect matches in the sequences involved in hybridization improve assay specificity without negative effects on reaction kinetics.

When added to the amplification reaction, the detector oligonucleotide reporter probe of the invention is converted to double-stranded form by hybridization and extension as illustrated in FIG. 1. Strand displacement by the polymerase also unfolds or linearizes the secondary structure and converts it to double-stranded form by synthesis of a complementary strand. The RERS, if present, also becomes double-stranded and cleavable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as; a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use in the detection of amplicons of other primer extension amplification methods (e.g., PCR, 3SR, TAS or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The signal primers hybridize to the target at least partially downstream from the PCR amplification primers, are displaced and are rendered double-stranded after hybridization to the detector oligonucleotide reporter probe and subsequent extension. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease that remains active through the high temperature phases of the PCR reaction could be present during amplification to provide a real-time assay. As in SDA systems, separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art (e.g., U.S. Pat. No. 5,928,907, U.S. patent application Ser. No. 09/196,123, filed Nov. 20, 1998, U.S. Pat. No. 6,216,049, and U.S. patent application Ser. No. 09/574,031, filed May, 19, 2000, all of which are specifically incorporated by reference herein) may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample that may interfere with detection of the signal or other aspects of the assay. An example of a solid phase system that can be used is an array format, such as those known in the art.

EXAMPLES

The following Examples illustrate specific embodiments of the invention described herein. As would be apparent to skilled artisans, various changes and modifications are possible, and are contemplated within the scope of the invention described.

EXAMPLE 1

Analytical Sensitivity

The amplification oligonucleotides shown in Table 1 were tested for amplification and detection of the rnpB target. Amplification reactions were conducted at 0, 10, 25, 50, 100, and 200 copies per reaction of cloned plasmid containing a C. pneumoniae, C. trachomatis or C. psittaci rnpB target insert. The amplification reactions were conducted at 52° C. under two buffer conditions. The final concentrations of the components in each buffer condition are described below.

Condition 1: 45 mM potassium phosphate (pH 7.6), 58 mM Bicine, 35 mM potassium hydroxide, 10% glycerol, 10% dimethylsulfoxide (DMSO), 5 mM magnesium acetate, 700 ng human placental DNA, 10 μg acetylated bovine serum albumin, 100 nM upstream primer (SEQ ID NO: 1), 500 nM downstream primer (SEQ ID NO: 3), 50 nM bumper primers (SEQ ID NOs: 5 and 7), 250 nM signal primer (SEQ ID NO: 9), 500 nM reporter probe (SEQ ID NO: 11), 0.1 mM dATP, 0.1 mM dGTP, 0.1 mM dTTP, 0.5 mM 2'-Deoxycytidine 5'-O-(1-Thiotriphosphate) S-isomer, and approximately 26.5 units BsoB1 and 8 units Bst polymerase.

Condition 2: 45 mM potassium phosphate (pH 7.6), 100 mM Bicine, 35 mM potassium hydroxide, 7% glycerol, 7% dimethylsulfoxide (DMSO), 5 mM magnesium acetate, 700 ng human placental DNA, 10 μg acetylated bovine serum albumin, 500 nM upstream primer (SEQ ID NO: 2), 100 nM downstream primer (SEQ ID NO: 4), 50 nM bumper primers (SEQ ID NOs: 6 and 8), 250 nM signal primer (SEQ ID NO: 10), 500 nM reporter probe (SEQ ID NO: 11), 0.1 mM dATP, 0.1 mM dGTP, 0.1 mM dTTP, 0.5 mM 2'-Deoxycytidine 5'-O-(1-Thiotriphosphate) S-isomer, and approximately 26.5 units BsoB1 and 8 units Bst polymerase.

In brief, target DNA was denatured for 5 minutes at 95° C. and cooled to room temperature prior to addition to a buffer containing the primers and bumpers. Incubation was continued at room temperature for 20 minutes, followed by incubation at 72° C. for 10 minutes to minimize potential false priming. Amplification was then initiated at 52° C. by transfer of a fixed volume of the priming mix to microtiter wells containing the amplification enzymes. Amplification and real time detection was carried out for 1 hour at a constant temperature of 52° C. Specific amplification products were detected by monitoring the change in fluorescence intensity associated with the hybridization of a reporter probe (SEQ ID NO: 11) to the complement of the appropriate signal primer (SEQ ID NO: 9 or 10), the subsequent extension of the signal primer complement and cleavage of the resultant double stranded product. The limit of detection (the lowest target level that yielded a positivity rate of 100%) was 100 copies per reaction for C. pneumoniae, 25 copies per reaction for C. trachomatis, and 50 copies per reaction for C. psittaci under both amplification conditions.

EXAMPLE 2

Evaluation of Primer Specificity

Primer specificity was evaluated using SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and the reaction conditions as described above in Example 1. Primer specificity was evaluated using fifteen different strains of C. trachomatis, six strains of C. pneumoniae, two strains of C. psittaci (Table 2). All of the strains tested positive for a calculated specificity of 100% under both amplification conditions.

TABLE 2

Chlamydiaceae Specificity Panel

| Species | Serovar/Strain | Strain # | Target Level |
|---|---|---|---|
| C. trachomatis | A | ATCC VR-571 | 500 EB/reaction |
| C. trachomatis | B | ATCC VR-573 | 500 EB/reaction |
| C. trachomatis | Ba | ATCC VR-347 | 500 EB/reaction |
| C. trachomatis | C | ATCC VR-572 | 500 EB/reaction |
| C. trachomatis | D | ATCC VR-885 | 500 EB/reaction |
| C. trachomatis | E | ATCC VR-348 | 500 EB/reaction |
| C. trachomatis | F | ATCC VR-346 | 500 EB/reaction |
| C. trachomatis | G | ATCC VR-878 | 500 EB/reaction |
| C. trachomatis | H | ATCC VR-879 | 500 EB/reaction |
| C. trachomatis | I | ATCC VR-880 | 500 EB/reaction |
| C. trachomatis | J | ATCC VR-886 | 500 EB/reaction |
| C. trachomatis | K | ATCC VR-887 | 500 EB/reaction |
| C. trachomatis | L1 | ATCC VR-901B | 500 EB/reaction |
| C. trachomatis | L2 | ATCC VR-902B | 500 EB/reaction |
| C. trachomatis | L3 | ATCC VR-903B | 500 EB/reaction |
| C. pneumoniae | AR-39 | ATCC 53592 | 500 EB/reaction |
| C. pneumoniae | TW-183 | ATCC VR-2282 | 500 EB/reaction |
| C. pneumoniae | CM-1 | ATCC VR-1360 | 2.5 TCID/reaction |
| C. pneumoniae | 2043 | ATCC VR-1355 | 2.5 TCID/reaction |
| C. pneumoniae | CDC/CWL-029 | ATCC VR-1310 | 2.5 TCID/reaction |
| C. pneumoniae | 2023 | ATCC VR-1356 | 2.5 TCID/reaction |
| C. psittaci | Cal-10 | BD+ 86-31306 | 500 EB/reaction |
| C. psittaci | Borg | ABi* 4094-032895 | 500 copies/reaction |

*Advanced Biotechnologies, Inc.
+BD Biosciences

EXAMPLE 3

Evaluation of Cross-Reactivity

Cross-reactivity was evaluated using SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and the reaction conditions as described above in Example 1. Cell lysates and genomic DNA from one hundred and five organisms were tested. Parallel reactions were performed with 250 copies of a plasmid containing a cloned fragment of the C. pneumoniae rnpB gene spiked into the sample to ensure that amplification reactions were not suppressed. No evidence of cross-reactivity was obtained with any of the 105 organisms tested (Table 3) with either SDA system.

TABLE 3

Chlamydiaceae Cross-Reactivity Panel

| Organism | Strain # | genomic equivalents per reaction |
|---|---|---|
| Acinetobacter calcoaceticus | ATCC 13339 | 1 × 10⁶ |
| Acinetobacter lwoffii | ATCC 19001 | 1 × 10⁶ |
| Actinomyces israelii | ATCC 10049 | 1 × 10⁶ |
| Adenovirus-5 | ABi* 74-070 | 1 × 10⁴ |
| Aeromonas hydrophila | ATCC 7966 | 1 × 10⁶ |
| Alcaligenes faecalis | ATCC 8750 | 1 × 10⁶ |
| Bacillus subtilis | ATCC 12100 | 1 × 10⁶ |
| Bacteroides fragilis | ATCC 25285 | 1 × 10⁶ |
| Blastomyces dermatitidis | ATCC 4292 | 1 × 10⁶ |
| Bordetella bronchiseptica | ATCC 10580 | 1 × 10⁶ |
| Bordetella parapertussis | ATCC 15311 | 1 × 10⁶ |
| Bordetella pertussis | ATCC 9797 | 1 × 10⁶ |
| Branhamella catarrhalis | ATCC 25285 | 1 × 10⁶ |
| Candida albicans | ATCC 44808 | 1 × 10⁶ |
| Candida glabrata | ATCC 90030 | 1 × 10⁶ |
| Candida tropicalis | ATCC 750 | 1 × 10⁶ |
| Citrobacter freundii | ATCC 8090 | 1 × 10⁶ |
| Clostridium perfringens | ATCC 13124 | 1 × 10⁶ |
| Coccidioides immitis | ATCC 7366 | 1 × 10⁶ |
| Corynebacterium diphtheriae | ATCC 11913 | 1 × 10⁶ |
| Corynebacterium jeikeium | ATCC 43734 | 1 × 10⁶ |
| Corynebacterium renale | ATCC 19412 | 1 × 10⁶ |
| Cryptococcus neoformans | ATCC 36556 | 1 × 10⁶ |
| Cytomegalovirus (AD-169) | ABi* 68-125 | 1 × 10⁴ |
| Edwardsiella tarda | ATCC 15469 | 1 × 10⁶ |
| Eikenella corrodens | ATCC 23834 | 1 × 10⁶ |
| Enterobacter aerogenes | ATCC 13048 | 1 × 10⁶ |
| Enterobacter cloacae | ATCC 13047 | 1 × 10⁶ |
| Enterococcus faecalis | ATCC 29212 | 1 × 10⁶ |
| Enterncoccus faecium | ATCC 19434 | 1 × 10⁶ |
| Enterovirus (Echovirus-11) | ABi* 74-084 | 1 × 10⁴ |
| Epstein-Barr Virus | Sigma 104H0854 | 2.6 × 10⁷ |
| Escherichia coli | ATCC 11775 | 1 × 10⁶ |
| Flavobacterium meningosepticum | ATCC 13253 | 1 × 10⁶ |
| Fusobacterium nucleatum | ATCC 25586 | 1 × 10⁶ |
| Gardnerella vaginalis | ATCC 14018 | 1 × 10⁶ |
| Gemella haemolysans | ATCC 10379 | 1 × 10⁶ |
| Group B Streptococcus | ATCC 12386 | 1 × 10⁶ |
| Haemophilus influenzae | ATCC 33533 | 1 × 10⁶ |
| Haemophilus parainfluenzae | ATCC 7901 | 1 × 10⁶ |
| Herpes Simplex Virus, type II | ABi* 4079-022895 | 2.3 × 10⁸ |
| Herpes Simplex Virus, type I | ABi* 68-097 | 1 × 10⁴ |
| Histoplasma capsulatum | ATCC 12700 | 1 × 10⁶ |
| HIV-I | ABi* 4314-042198 | 2.5 × 10⁶ |
| HPV type 16 | ATCC 45113D | 4.7 × 10⁶ |
| HPV type 18 | ATCC 45152D | 1.2 × 10⁶ |
| Influenza virus A (PR8) | BD+ 940422 | 2.25 × 10³ |
| Influenza virus B (HK/5/72) | BD+ 4356 | 7.25 × 10³ |
| Kingella kingae | ATCC 23330 | 1 × 10⁶ |
| Klebsiella pneumoniae ssp. ozaenae, type 4 | ATCC 11296 | 1 × 10⁶ |
| Klebsiella pneumoniae ssp. pneumoniae | ATCC 13883 | 1 × 10⁶ |
| Lactobacillus acidophilus | ATCC 4356 | 1 × 10⁶ |
| Lactobacillus brevis | ATCC 14869 | 1 × 10⁶ |
| Legionella micdadei | ATCC 33204 | 1 × 10⁶ |
| Legionella pneumophila | ATCC 33152 | 1 × 10⁶ |
| Listeria monocytogenes | ATCC 7644 | 1 × 10⁶ |
| Mobiluncus mulerieris | ATCC 35243 | 1 × 10⁶ |
| Moraxella lucanata | ATCC 17967 | 1 × 10⁶ |
| Moraxella osloensis | ATCC 19976 | 1 × 10⁶ |
| Morganella morganii | ATCC 25830 | 1 × 10⁶ |
| Mycobacterium avium | ATCC 25291 | 1 × 10⁶ |
| Mycobacterium gordonae | ATCC 14470 | 1 × 10⁶ |
| Mycobacterium intracellulare | ATCC 13950 | 1 × 10⁶ |
| Mycobacterium smegmatis | ATCC 19420 | 1 × 10⁶ |
| Mycobacterium tuberculosis | ATCC 27294 | 1 × 10⁶ |
| Mycoplasma genitalium | ATCC 33530 | 1 × 10⁵ |
| Mycoplasma hominis | ATCC 23114 | 1 × 10⁵ |
| Mycoplasma pneumoniae | ATCC 63-030 | 1 × 10⁵ |
| Neisseria cinerea | ATCC 14685 | 1 × 10⁶ |
| Neisseria gonorrhoeae | ATCC 19424 | 1 × 10⁶ |
| Neisseria meningitidis | ATCC 13077 | 1 × 10⁶ |
| Neisseria mucosa | ATCC 19696 | 1 × 10⁶ |
| Neisseria polysaccharea | ATCC 43768 | 1 × 10⁶ |
| Parainfluenza I virus (Sendai) | BD+ 951010 | 1.5 × 10³ |
| Peptostreptococcus anaerobius | ATCC 27337 | 1 × 10⁶ |
| Peptostreptococcus asaccharolyticus | ATCC 29743 | 1 × 10⁶ |
| Peptostreptococcus productus | ATCC 27340 | 1 × 10⁶ |
| Plesiomonas shigelloides | ATCC 14029 | 1 × 10⁶ |
| Porphyromonas asaccharolytica | ATCC 25260 | 1 × 10⁶ |
| Prevotella melaninogenicus | ATCC 25845 | 1 × 10⁶ |
| Prevotella oralis | ATCC 33269 | 1 × 10⁶ |
| Propionibacterium acnes | ATCC 6919 | 1 × 10⁶ |
| Proteus mirabilis | ATCC 29906 | 1 × 10⁶ |
| Providencia stuartii | ATCC 35031 | 1 × 10⁶ |

TABLE 3-continued

Chlamydiaceae Cross-Reactivity Panel

| Organism | Strain # | genomic equivalents per reaction |
|---|---|---|
| Pseudomonas aeruginosa | ATCC 27853 | $1 \times 10^6$ |
| Resp. Syncytial virus, Long strain | ABi* 74-093 | $1 \times 10^4$ |
| Rhinovirus | ABI* 80-015 | $2.5 \times 10^3$ |
| Salmonella choleraesuis serotype enteritidis | ATCC 13076 | $1 \times 10^6$ |
| Salmonella choleraesuis serotype typhi | ATCC 19430 | $1 \times 10^6$ |
| Salmonella minnesota | ATCC 9700 | $1 \times 10^6$ |
| Salmonella typhimurium | ATCC 13311 | $1 \times 10^6$ |
| Serratia marcescens | ATCC 8100 | $1 \times 10^6$ |
| Staphylococcus aureus, protein A-producing | ATCC 12598 | $1 \times 10^6$ |
| Staphylococcus aureus, non-protein A-producing | ATCC 25923 | $1 \times 10^6$ |
| Staphylococcus epidermidis | ATCC E155 | $1 \times 10^6$ |
| Stenotrophomonas maltophilia | ATCC 13637 | $1 \times 10^6$ |
| Streptococcus mitis | ATCC 6249 | $1 \times 10^6$ |
| Streptococcus mutans | ATCC 25175 | $1 \times 10^6$ |
| Streptococcus pneumoniae | ATCC 6303 | $1 \times 10^6$ |
| Streptococcus pyogenes | ATCC 19615 | $1 \times 10^6$ |
| Streptomyces griseus | ATCC 10137 | $1 \times 10^6$ |
| Trichomonas vaginalis | ATCC 30001 | $1 \times 10^6$ |
| Ureaplasma urealyticum | ATCC 27618 | $1 \times 10^5$ |
| Vibrio parahaemolyticus | ATCC 17802 | $1 \times 10^6$ |
| Yersinia enterocolitica | ATCC 27729 | $1 \times 10^6$ |

*Advanced Biotechnologies, Inc.
+BD Biosciences

While the invention has been described with some specificity, modifications apparent to those of ordinary skill in the art may be made without departing from the scope of the invention. Various features of the invention are set forth in the following claims.

---

What is claimed is:

1. An oligonucleotide consisting of a target binding sequence selected from the group consisting of the target binding sequences of CGLP 1.0 (SEQ ID NO: 1), Rnp LP (SEQ ID NO: 2), CGRP1.0 (SEQ ID NO: 3) and Rnp RP (SEQ ID NO: 4), and optionally, a sequence required for an amplification reaction.

2. The oligonucleotide of claim 1 wherein the sequence required for the amplification reaction is a restriction endonuclease recognition site that is nickable by a restriction endonuclease.

3. The oligonucleotide of claim 2 selected from the group consisting of CGLP1.0 (SEQ ID NO: 1), Rnp LP (SEQ ID NO: 2), CGRP1.0 (SEQ ID NO: 3) and Rnp RP (SEQ ID NO: 4).

4. An oligonucleotide selected from the group consisting of CGLB1.0 (SEQ ID NO: 5), Rnp LB (SEQ ID NO: 6), CGRB1.0 (SEQ ID NO: 7) and Rnp RB (SEQ ID NO: 8).

5. An oligonucleotide selected from the group consisting of CGA1.0 (SEQ ID NO: 9), a nucleic acid complementary to CGA1.0 (SEQ ID NO: 9), Rnp AD (SEQ ID NO: 10) and a nucleic acid complementary to Rnp AD (SEQ ID NO: 10).

6. The oligonucleotide of claim 5 wherein said oligonucleotide comprises an indirectly detectable marker.

7. The oligonucleotide of claim 6 wherein said indirectly detectable marker is an adapter sequence.

8. A pair of amplification primers comprising:
   a) a first primer consisting of a target binding sequence selected from the group consisting of the target binding sequences of CGLP1.0 (SEQ ID NO: 1) and Rnp LP (SEQ ID NO: 2), and, optionally, a sequence required for an amplification reaction, and;
   b) a second primer consisting of a target binding sequence selected from the group consisting of the target binding sequences of CGRP1.0 (SEQ ID NO: 3) and Rnp RP (SEQ ID NO: 4), and, optionally, a sequence required for an amplification reaction.

9. The pair of amplification primers of claim 8 wherein the sequence required for the amplification reaction is a restriction endonuclease recognition site that is nickable by a restriction endonuclease.

10. The pair of amplification primers of claim 9 wherein said first primer is selected from the group consisting of CGLP1.0 (SEQ ID NO: 1) and Rnp LP (SEQ ID NO: 2) and said second primer is selected from the group consisting of CGRP1.0 (SEQ ID NO: 3) and Rnp RP (SEQ ID NO: 4).

11. The pair of amplification primers of claim 9 wherein said first primer is Rnp LP (SEQ ID NO: 2) and said second primer is Rnp RP (SEQ ID NO: 4).

12. A kit comprising:
   a) one or more primers selected from the group consisting of CGLP1.0 (SEQ ID NO: 1) and Rnp LP (SEQ ID NO: 2),
   b) one or more primers selected from the group consisting of CGRP1.0 (SEQ ID NO: 3) and Rnp RP (SEQ ID NO: 4),
   c) one or more bumpers selected from the group consisting of CGLB1.0 (SEQ ID NO: 5), Rnp LB (SEQ ID NO: 6), CGRB1.0 (SEQ ID NO: 7) and Rnp RB (SEQ ID NO: 8), and
   d) one or more signal primers selected from the group consisting of CGA1.0 (SEQ ID NO: 9), a nucleic acid complementary to CGA1.0 (SEQ ID NO: 9), Rnp AD (SEQ ID NO: 10) and a nucleic acid complementary to Rnp AD (SEQ ID NO: 10).

13. The kit of claim 12 wherein said one or more signal primers comprises an indirectly detectable marker.

14. The kit of claim 13 wherein said indirectly detectable marker is an adapter sequence.

15. The kit of claim 14 further comprising a reporter probe of SEQ ID NO:11.

16. The kit of claim 12 further comprising:
   e) a pair of primers specific for the amplification of a nucleic acid sequence specific for *Bordetella pertussis;*
   f) a pair of primers specific for the amplification of a nucleic acid sequence specific for *Mycoplasma pneumoniae*; and
   g) a pair of primers specific for the amplification of a nucleic acid sequence specific for *Legionella pneumophila.*

17. A method for detecting the presence or absence of organisms of the Chlamydiaceae family in a sample, said method comprising:
   a) treating said sample using a pair of nucleic acid primers in a nucleic acid amplification reaction wherein a first primer is selected from the group consisting of CGLP1.0 (SEQ ID NO: 1) and Rnp LP (SEQ ID NO: 2), and said second primer is selected from the group consisting of CGRP1.0 (SEQ ID NO: 3) and Rnp RP (SEQ ID NO: 4), and
   b) detecting any amplified nucleic acid product, wherein detection of amplified product indicates presence of organisms of the Chlamydiaceae family.

18. The method of claim 17 wherein said nucleic acid amplification reaction is a Strand Displacement Amplification (SDA) reaction.

19. The method of claim 18 wherein said SDA reaction utilizes a first bumper selected from the group consisting of CGLB1.0 (SEQ ID NO: 5) and Rnp LB (SEQ ID NO: 6), and a second bumper selected from the group consisting of CGRB1.0 (SEQ ID NO: 7) and Rnp RB (SEQ ID NO: 8).

20. The method of claim 17 wherein indirectly detecting said amplified nucleic acid product is conducted by hybridizing said amplified nucleic acid product with a signal primer selected from the group consisting of CGA1.0 (SEQ ID NO: 9), a nucleic acid complementary to CGA1.0 (SEQ ID NO: 9), Rnp AD (SEQ ID NO: 10) and a nucleic acid complementary to Rnp AD (SEQ ID NO: 10).

21. The method of claim 18 wherein said SDA reaction is a thermophilic Strand Displacement Amplification (tSDA) reaction.

22. The method of claim 21 wherein said tSDA reaction is a homogeneous fluorescent real time tSDA reaction.

23. A method for amplifying a target nucleic acid sequence from an organism of the Chlamydiaceae family comprising:
   a) hybridizing to the nucleic acid
      i) a first amplification primer selected from the group consisting of a target binding sequence of CGLP1.0 (SEQ ID NO: 1) and a target binding sequence of Rnp LP (SEQ ID NO: 2), and, optionally, a sequence required for an amplification reaction, and
      ii) a second amplification primer selected from the group consisting of a target binding sequence of CGRP1.0 (SEQ ID NO: 3) and a target binding sequence of Rnp RP (SEQ ID NO: 4), and, optionally, a sequence required for the amplification reaction, and;
   b) extending the hybridized first and second amplification primers on the target nucleic acid sequence whereby the target nucleic acid sequence is amplified.

24. The method of claim 23 further comprising indirectly detecting the amplified target nucleic acid by hybridization to a signal primer.

25. The method of claim 24 wherein the signal primer is selected from the group consisting of CGA1.0 (SEQ ID NO: 9), a nucleic acid complementary to CGA1.0 (SEQ ID NO: 9), Rnp AD (SEQ ID NO: 10) and a nucleic acid complementary to Rnp AD (SEQ ID NO: 10).

26. The method of claim 23 wherein the sequence required for the amplification reaction is a recognition site for a restriction endonuclease that is nicked by the restriction endonuclease during Strand Displacement Amplification (SDA).

27. The method of claim 26 wherein the first amplification primer is selected from the group consisting of CGLP1.0 (SEQ ID NO: 1) and Rnp LP (SEQ ID NO: 2), and the second amplification primer is selected from the group consisting of CGRP1.0 (SEQ ID NO: 3) and Rnp RP (SEQ ID NO: 4).

28. The method of claim 27 wherein the hybridized first and second amplification primers are displaced from the target nucleic acid by extension of a first bumper primer selected from the group consisting of CGLB1.0 (SEQ ID NO: 5) and Rnp LB (SEQ ID NO: 6), and a second bumper selected from the group consisting of CGRB1.0 (SEQ ID NO: 7) and Rnp RB (SEQ ID NO: 8).

29. The method of claim 23 wherein the target nucleic acid is amplified by the Polymerase Chain Reaction.

30. The method of claim 26 wherein said SDA reaction is a thermophilic Strand Displacement Amplification (tSDA) reaction.

31. The method of claim 30 wherein said tSDA reaction is a homogeneous fluorescent real time tSDA reaction.

* * * * *